United States Patent
Ho (10) Patent No.: US 10,624,615 B2
(45) Date of Patent: Apr. 21, 2020

(54) APPARATUS AND METHOD FOR COLLECTING AND ISOLATING CELLS

(71) Applicant: Stephen S Ho, Houston, TX (US)

(72) Inventor: Stephen S Ho, Houston, TX (US)

( * ) Notice: Subject to any disclaimer, the term of this patent is extended or adjusted under 35 U.S.C. 154(b) by 76 days.

(21) Appl. No.: 15/726,981

(22) Filed: Oct. 6, 2017

(65) Prior Publication Data

US 2019/0105022 A1    Apr. 11, 2019

(51) Int. Cl.
*A61B 10/00* (2006.01)
*A61B 10/02* (2006.01)
*C12M 1/00* (2006.01)
*C12M 1/26* (2006.01)

(52) U.S. Cl.
CPC .......... *A61B 10/02* (2013.01); *A61B 10/0045* (2013.01); *A61B 10/0096* (2013.01); *A61B 10/0283* (2013.01); *C12M 1/26* (2013.01); *C12M 47/02* (2013.01); *C12M 47/04* (2013.01)

(58) Field of Classification Search
CPC . A61B 10/02; A61B 10/0283; A61B 10/0096; A61B 10/0045; C12M 47/02; C12M 47/04; C12M 1/26
See application file for complete search history.

(56) References Cited

U.S. PATENT DOCUMENTS

| | | |
|---|---|---|
| 4,020,831 A | 5/1977 | Adler |
| 4,958,622 A * | 9/1990 | Selenke ............. A61B 10/0045 600/578 |
| 5,577,513 A | 11/1996 | Van Vlasseleaer |
| D401,324 S | 11/1998 | Hjertman |
| D445,176 S | 7/2001 | Landers |
| 6,398,972 B1 | 6/2002 | Blasetti et al. |
| 6,402,721 B1 | 6/2002 | Lo |
| 6,616,639 B2 | 9/2003 | Gagnieux et al. |
| D483,861 S | 12/2003 | Law |
| 6,729,370 B2 | 5/2004 | Norton |
| 6,936,034 B2 | 8/2005 | Watkins |
| D578,210 S | 10/2008 | Muta |
| D609,333 S | 2/2010 | Holmes |

(Continued)

FOREIGN PATENT DOCUMENTS

EP     2628484 A1    8/2013
WO   WO2005105121 A1   11/2005

OTHER PUBLICATIONS

International Search Report for PCT/US2018/54713, mailed by International Search Authority dated Dec. 27, 2018, one page, attached.

(Continued)

*Primary Examiner* — Navin Natnithithadha
*Assistant Examiner* — Andrey Shostak
(74) *Attorney, Agent, or Firm* — Whittaker Law Firm; Malcolm E. Whittaker (57) ABSTRACT

A cell collection apparatus for collecting and isolating a sample having a sample collection section with a reservoir barrel, a fitting slidably movable within the reservoir barrel, and a proximal attachment, the proximal attachment located on the distal side of the fitting; a detachable section having a plunger, the plunger detachably connected to the proximal attachment by a distal attachment; and whereby after detachment of the detachable section, the sample collection section is centrifuged to separate the sample into its components.

12 Claims, 11 Drawing Sheets

(56) References Cited

U.S. PATENT DOCUMENTS

| | | |
|---|---|---|
| D618,347 S | 6/2010 | Bradshaw |
| 7,976,506 B2 | 7/2011 | Vitullo |
| 8,337,468 B1 | 12/2012 | Reis |
| D689,601 S | 9/2013 | Black |
| D741,476 S | 10/2015 | Hiraoka |
| D755,955 S | 5/2016 | Kawamura |
| D770,612 S | 11/2016 | Green |
| D775,325 S | 12/2016 | Larson |
| D830,542 S | 10/2018 | Walker |
| D834,182 S | 11/2018 | Reynolds |
| D837,983 S | 1/2019 | Fangrow |
| D844,777 S | 4/2019 | Combes |
| 2004/0092884 A1* | 5/2004 | Rimlinger ............ A61M 5/326 604/198 |
| 2005/0123895 A1 | 6/2005 | Freund |
| 2007/0280959 A1 | 12/2007 | Meury et al. |
| 2008/0281266 A1* | 11/2008 | Walton ............... A61M 5/5013 604/110 |
| 2009/0156962 A1* | 6/2009 | Yong ................. A61B 10/0045 600/569 |
| 2010/0286622 A1* | 11/2010 | Liu ..................... A61M 5/3234 604/196 |
| 2011/0086426 A1* | 4/2011 | Freund .................. C12M 45/05 435/379 |
| 2012/0082652 A1* | 4/2012 | Sengun ................. A61M 1/029 424/93.72 |
| 2014/0350517 A1* | 11/2014 | Dominguez ...... A61M 5/31501 604/506 |
| 2015/0044179 A1 | 2/2015 | Saeki |
| 2015/0230781 A1* | 8/2015 | Loktionov ............ A61B 10/04 600/572 |
| 2018/0010086 A1* | 1/2018 | Gupta ................... C12M 47/04 |

OTHER PUBLICATIONS

Notice of References Cited in Co-Pending Design U.S. Appl. No. 29/681,032 (two pages) sent with Notice of Allowance and Fee(s) Due dated Jan. 13, 2020.

* cited by examiner

APPARATUS AND METHOD FOR COLLECTING AND ISOLATING CELLS

STATEMENT REGARDING FEDERALLY SPONSORED RESEARCH

Not Applicable.

TECHNICAL FIELD OF THE INVENTION

The technical field of this disclosure relates to the collection and isolation of cells collected from a patient.

BACKGROUND OF THE INVENTION

Collection and isolation of a person's own cells and the reintroduction of the isolated cells can have beneficial therapeutic results. For example, platelet-rich-plasma (PRP), stem cells and fat can be collected from a patient, isolated and then returned to the patient's own body to provide beneficial therapeutic results.

In order to obtain samples of stem cells or PRP, a sample of whole blood is collected from the patient. Similarly, to obtain fat for use in the patient, a fat grafting procedure transfers fat from areas where the patient has excess fat, such as the outer thigh, abdomen, or buttocks and injects it into areas that may be lacking volume, i.e. volume deficient areas.

Typical difficulties with these types of processes include cell necrosis. Thus, it is important to have processes that both collect and isolate the desired cells and also mitigates that risk that the cells that have been isolated die or are damaged, i.e. cell necrosis.

As disclosed and taught in the following materials, a variety of methods and apparatus/systems may be used in the isolation of stem cells, platelets and fat cells.

BACKGROUND

Other methods of isolating the patient's cells may also provide therapeutic benefit.

For example, U.S. Pat. No. 6,398,972, "Method of Producing Platelet Rich Plasma and/or Platelet Concentration," issued to Blasetti et al., on Jun. 4, 2002, discloses platelet rich plasma and/or platelet concentrate prepared by placing whole blood in a first chamber of a sterile processing disposable having two chambers. The processing disposable is subjected to a first centrifugation to separate red blood cells, and the resulting platelet rich plasma supernatant is decanted to the second chamber. The processing disposable is subjected to a second centrifugation to concentrate platelets. A volume of platelet poor plasma supernatant in the second chamber is removed, and the platelets are re-suspended in the remaining plasma. The second chamber may contain anticoagulant to preclude aggregation of the platelets.

As another example, International Application published under the Patent Cooperation Treaty under International Publication No. WO2005105121A1 on Nov. 10, 2005, by Meury et al., discloses the use of the content of platelets or platelet rich plasma (PRP) obtained by disruption of their membranes for the preparation of an agent for the treatment of bone, cartilage or skin.

Another example, U.S. Patent Application Publication No. 2007/0280959, published on Dec. 6, 2007, by Meury et al., discloses a new use for the contents of platelets or platelet rich plasma (PRP) obtained by disruption of their membranes for the preparation of an agent for the treatment of bone, cartilage or skin.

Another example, European Patent Office Publication EP2628484A1, published on Aug. 21, 2013, by Agut Sanchez, et al., discloses a pharmaceutical composition for oral administration comprising platelet-rich plasma and uses thereof. The invention also relates to orally administered cosmetic compositions and nutritional compositions comprising platelet-rich plasma.

Yet another example, U.S. Patent Application Publication 2015/0044179A1, by Masanori Saeki, discloses a cell preparation useful for treatment of diseases in bone joints and repairing muscles which have been degenerated or damaged. And, also discloses a cell preparation for treatment of diseases in bone joints which comprises a fat cell, and a cell preparation for repairing muscles which comprises a fat cell and a mesodermal stem cell.

SUMMARY OF THE INVENTION

A cell collection apparatus for collecting and isolating a sample having a sample collection section with a reservoir barrel, a fitting slidably movable within the reservoir barrel, and a proximal attachment, the proximal attachment located on the distal side of the fitting; a detachable section having a plunger, the plunger detachably connected to the proximal attachment by a distal attachment; and whereby after detachment of the detachable section, the sample collection section is centrifuged to separate the sample into its components.

These and other embodiments will be more fully appreciated from the description below.

DESCRIPTION OF THE PREFERRED EMBODIMENTS

Corresponding reference numbers indicate corresponding parts throughout the several views of the drawings and specification.

Figure 1A:
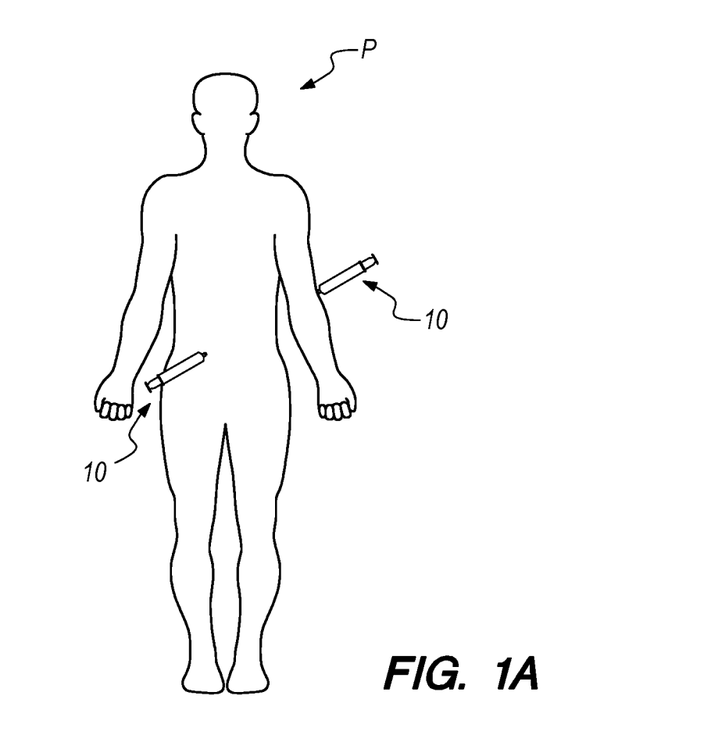
FIG. 1A illustrates a patient having cell sample(s) collected.

FIG. 1A illustrates a patient P having her cells collected using a cell collection apparatus 10 from various different portions of her body. As illustrated in FIG. 1A, cell collection apparatus 10 could be used to collect cells by drawing whole blood from patient P's veins. Typically, a needle is used for venipuncture. Similarly, cell collection apparatus 10 could also be used to collect a tissue sample of patient P's fat cells. Typically, a cannula is used for fat collection. As illustrated in FIG. 1A, fat cells could be collected from patient P's abdomen or others areas of the body with sufficient fatty deposits. Patient P's tissue sample could then be centrifuged thereby isolating different cell types. As an example, a whole blood sample could be collected from a patient. The whole blood sample could then be centrifuged thereby separating the whole blood sample into its component parts; such as plasma and platelets. Similarly, human fat tissue can be collected and centrifuge to isolate different cells types, such as stem cells and other cells. As discussed above, it can be beneficial for a patient to have a tissue sample collected from her body, certain desirable cells isolated, and the desirable cells re-introduced into the patient's body. For example, it is believed that stem cells isolated from a patient can be re-injected back into a patient to speed healing or provide other health advantages. As an example, the re-injection of a patient's own fatty cells into the patient's cheeks can improve a patient's appearance and provide a more youthful appearance. A variety of health and cosmetic benefits can be achieved by re-injecting a patient's own cells. However, in order to improve these results, it is desirable to isolate the cells that are beneficial. Phrased differently, certain cells may have beneficial effects when re-injected and encourage repair and regeneration of the patient's body. As an example, re-injection of a patient's stem cells is believed to improve healing of the patient's injured joints.

Figure 1B:
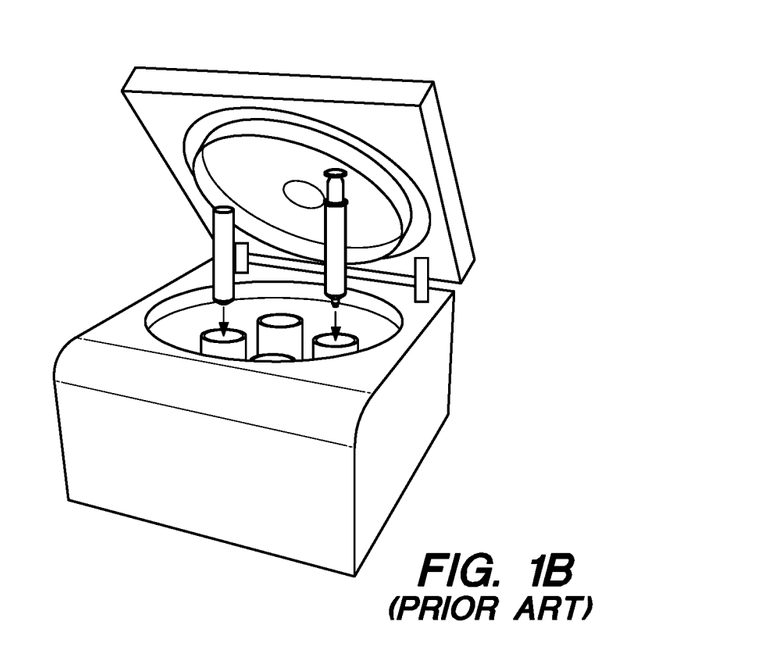
FIG. 1B illustrates a perspective view of a conventional centrifuge centrifuging a sample that has been collected using a conventional syringe, the sample is illustrated on the left as being transferred into a conventional test tube and then placed in the centrifuge or the sample could be retained in the syringe and placed in the centrifuge.

FIG. 1B illustrates a view of a conventional centrifuge centrifuging a sample that has been collected using a conventional syringe, in the example seen on the left of the centrifuge; the sample is illustrated as being transferred into a conventional test tube for centrifuging. Alternatively, as seen on the right side of the centrifuge, the sample could be retained in the syringe. FIG. 1B illustrates that if the sample is retained in the syringe during centrifuging, the syringe is placed such that the needle-end of the syringe is placed downwardly into the centrifuge. This is undesirable because the conventional syringe is more prone to leaking when faced downwardly.

Figure 2A:
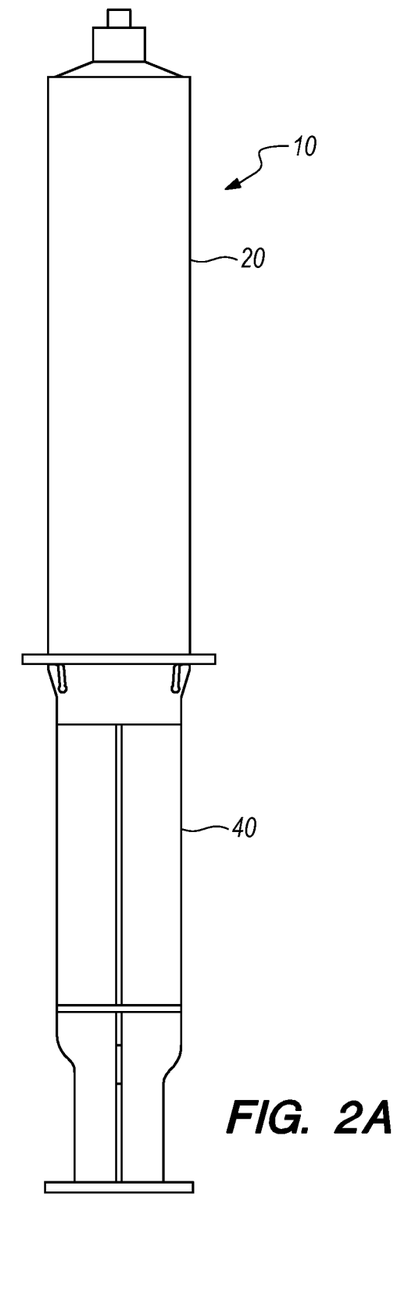
FIG. 2A illustrates a plan view of a cell collection apparatus.

FIG. 2A illustrates cell collection apparatus 10. Cell collection apparatus 10 comprises sample collection section 20 and detachable section 40.

Figure 2B:
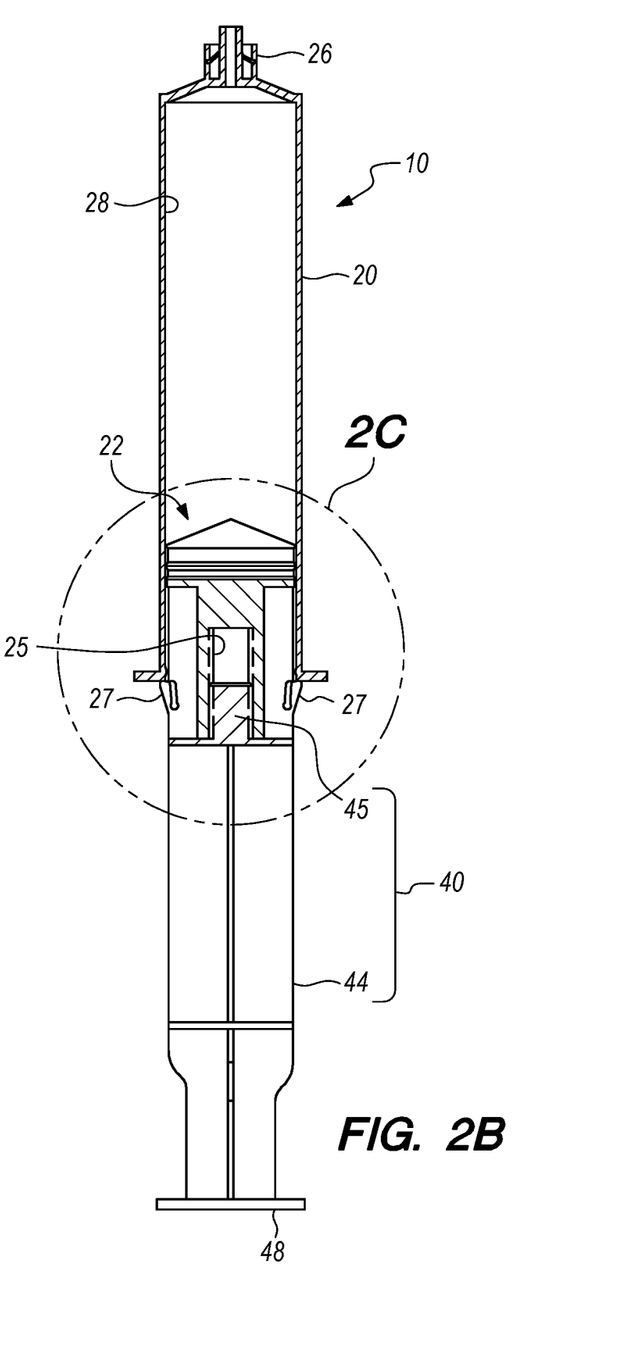
FIG. 2B illustrates a cross-sectional plan view of the cell collection apparatus.

FIG. 2B illustrates a cross-sectional plan view of the cell collection apparatus 10. Sample collection section 20 comprises fitting 22, proximal attachment 25, nipple 26, and reservoir 28. Fitting 22 is slidably disposed within reservoir 28. Detachable section 40 comprises a plunger 44, a distal attachment 45, and a handle 48. In a preferred embodiment, sample collection section 20 further comprises clips 27.

Figure 2C:
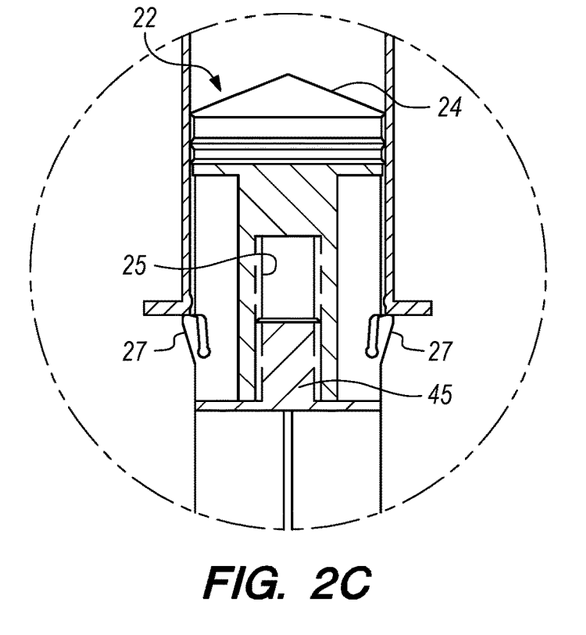
FIG. 2C illustrates a cross-sectional plan detailed view of the cell collection apparatus seen in FIG. 2B.

FIG. 2C illustrates a cross-sectional plan detailed view of the cell collection apparatus 10 seen in FIG. 2B. FIG. 2C further illustrates that clips 27 are preferably formed of resilient plastic and bias outwardly such that clips 27 holds sample collection section 20 and overcomes the negative pressure that occurs when fluid is drawn into reservoir 28. In this way, clips 27 temporarily immobilize fitting 22 and temporarily "lock" it into place. Preferably, clips 27 are sufficiently pliable that a user can gently urge clips 27 inwardly thereby permitting fitting 22 to move, i.e. "unlock," and urge fluid out of reservoir 28 through nipple 26. Preferably, proximal attachment 25 is threaded and distal attachment 45 has a corresponding thread thereon such that distal attachment 45 and proximal attachment 25 are detachably and threadedly connected. However, other means of detachably connecting sample collection section 20 to detachable section 40 may be employed. For example, section 20 and section 40 could be detachably connected by means of a pressure fitting such that proximal attachment 25 is sufficiently malleable and slightly narrower than distal attachment 45 such that the two are detachably connected. Other non-limiting examples of structure to detachably connect section 20 and section 40 are a male-female connector, a reverse male-female connector, snaps, clips, or magnetically detachably connecting sections 20 and section 40.

Figure 2D:
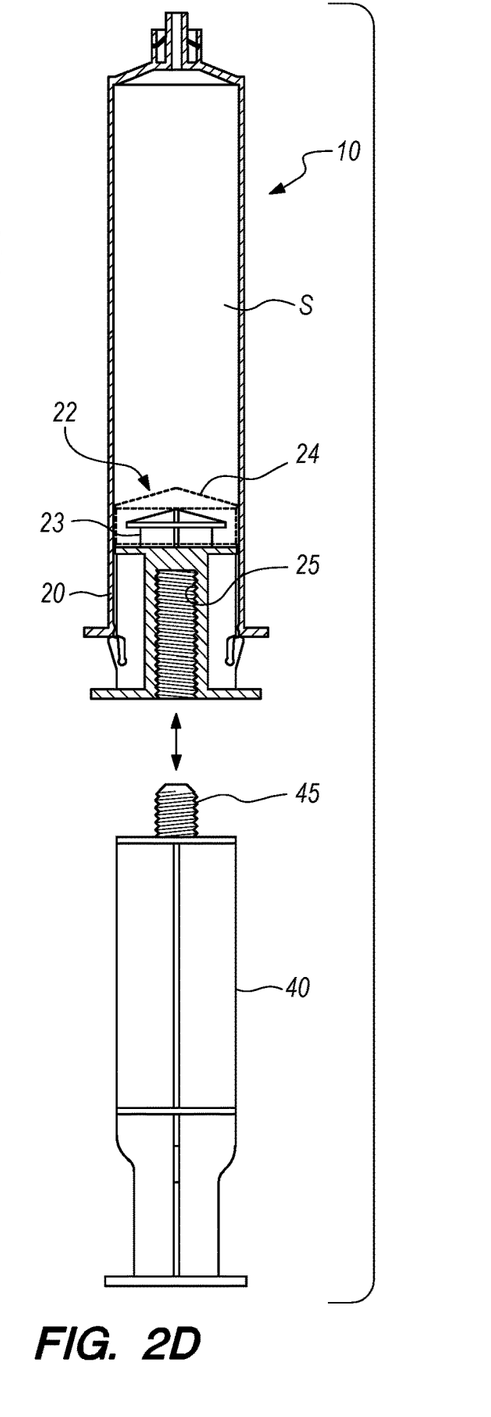
FIG. 2D illustrates a plan cross-sectional view of the cell collection apparatus seen after the detachable section is detached from the sample collection section of the cell collection apparatus

FIG. 2D illustrates a cross-sectional plan view of the cell collection apparatus 10 seen in FIG. 2B after the detachable section 40 is detached from the sample collection section 20 of the cell collection apparatus 10. FIG. 2D illustrates the fitting 22 comprising a post 23 and a seal 24. FIG. 2D further illustrates that sample collection section 20 could contain virtually all types of bodily fluids. For example, section 20 could contain blood, fat and other samples of body fluids.

Figure 3A:
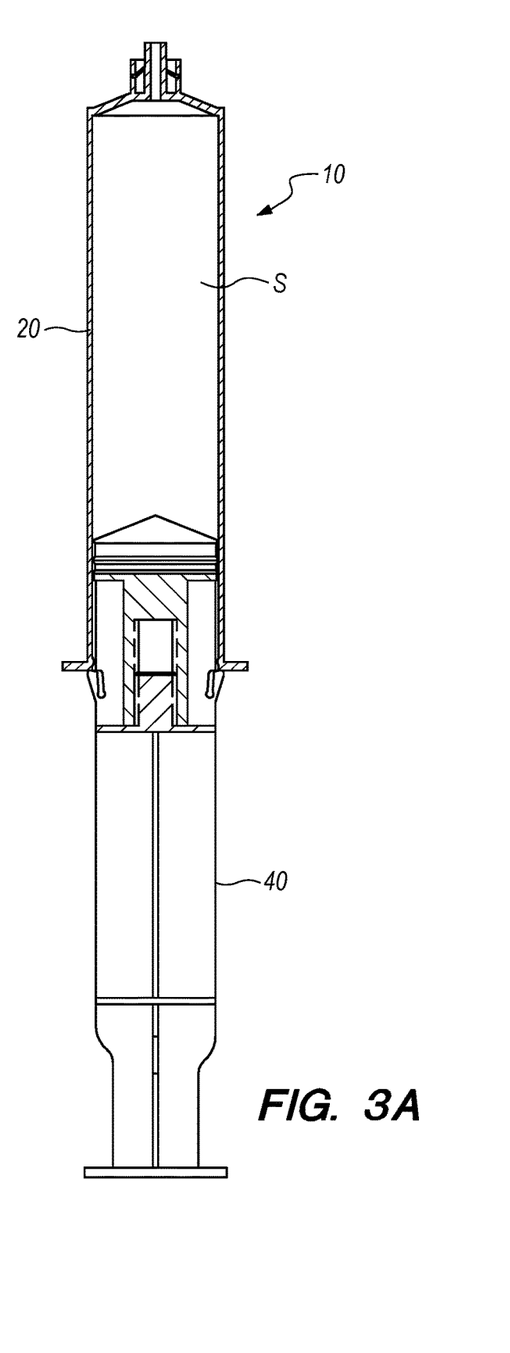
FIG. 3A illustrates a plan cross-sectional view the cell collection apparatus after a cell sample has been collected within the sample collection section.

FIG. 3A illustrates the cell collection apparatus 10 containing a sample S of the patient P's cells.

Figure 3B:
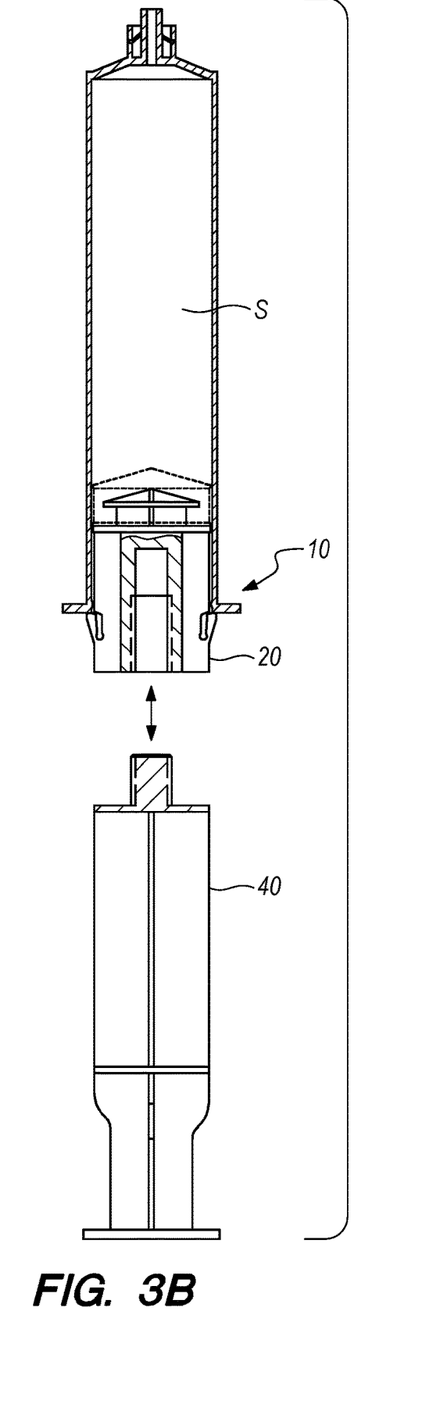
FIG. 3B illustrates a plan cross-sectional view the post-sample collection cell collection apparatus with the detachable section detached from the sample collection section after a cell sample has been collected.

FIG. 3B illustrates the cell collection apparatus 10 with detachable section 40 detached from sample collection section 20. As discussed above, sample collection section 20 contains sample S of patient P's cells. Examples of cell samples are blood, blood products, fat, fat tissue, fat tissue products, and, other cells, and cell products.

Figure 4A:
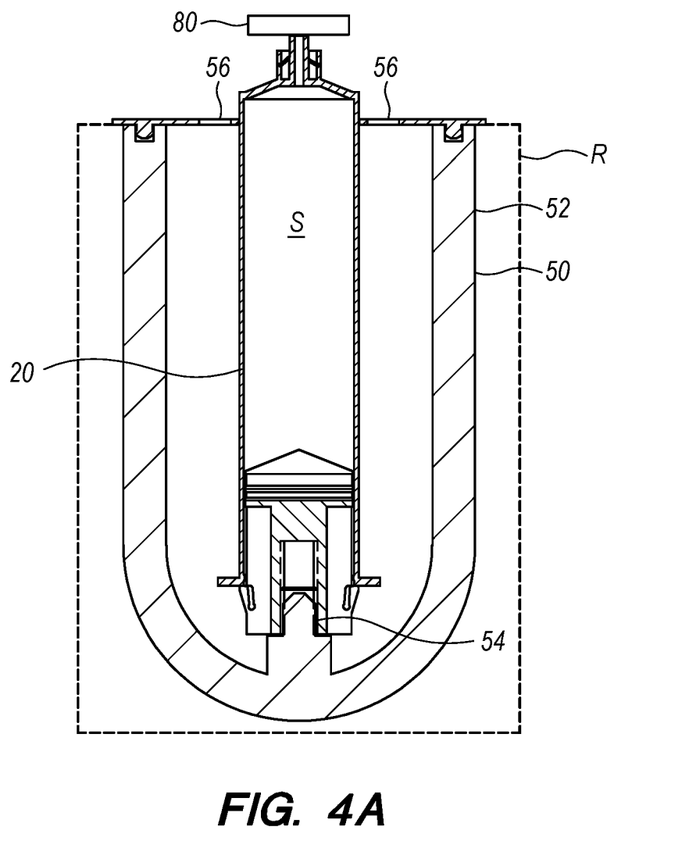
FIG. 4A illustrates a plan cross-sectional view of a retaining cup.

FIG. 4A illustrates the sample collection section 20 of cell collection apparatus 10 positioned in a retainer 50 of a centrifuge R. Retainer 50 comprises cup 52, support 54, and stabilizers 56. As illustrated in FIG. 4A, the sample collection section 20 of cell collection apparatus 10 is preferably slidably positioned on support 54 and stabilizers 56 are positioned to minimize relative movement of sample collection section 20 during centrifuging by centrifuge R. However, any structure that holds sample collection section 20 and allows centrifuging of sample S is appropriate. For example, a concave or convex shape disposed at the bottom of cup 52 could replace support 54. For example, the bottom surface of sample collection section 20 could concavely shaped to fit within a protrusion in the bottom of cup 52 or the bottom surface of sample collection section 20 could be convex and the bottom of cup 52 could be concave. Preferably, cap 80 is also used to reduce escape of sample S.

Figure 4B:
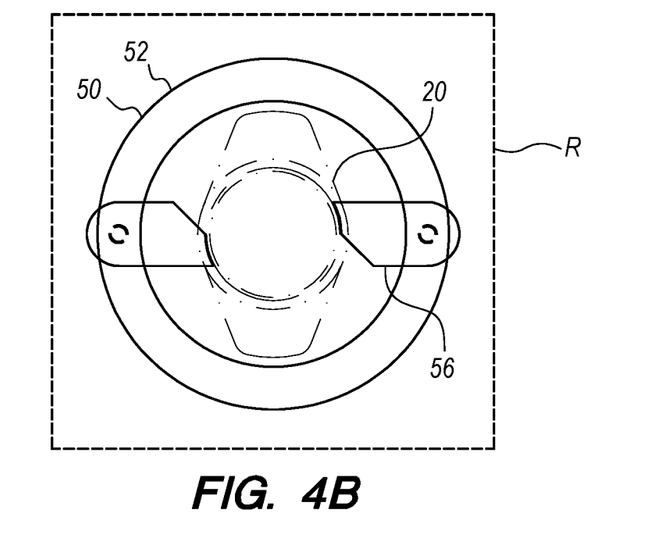
FIG. 4B illustrates a top view of the retaining cup.

FIG. 4B illustrates stabilizers 56 supporting sample collection section 20. Stabilizers 56 minimize motion of sample collection section 20 relative to retainer 50 during centrifuging.

Preferably, centrifuge R rotates sample collection section 20 about a fixed axis. As section 20 spins, centrifugal acceleration causes denser substances to move outward in a radial direction. As such, when section 20 is centrifuged, the denser particles of sample S settle to the bottom of the section 20, while the lower density components of sample S rise to the top of sample S.

Figure 4C:
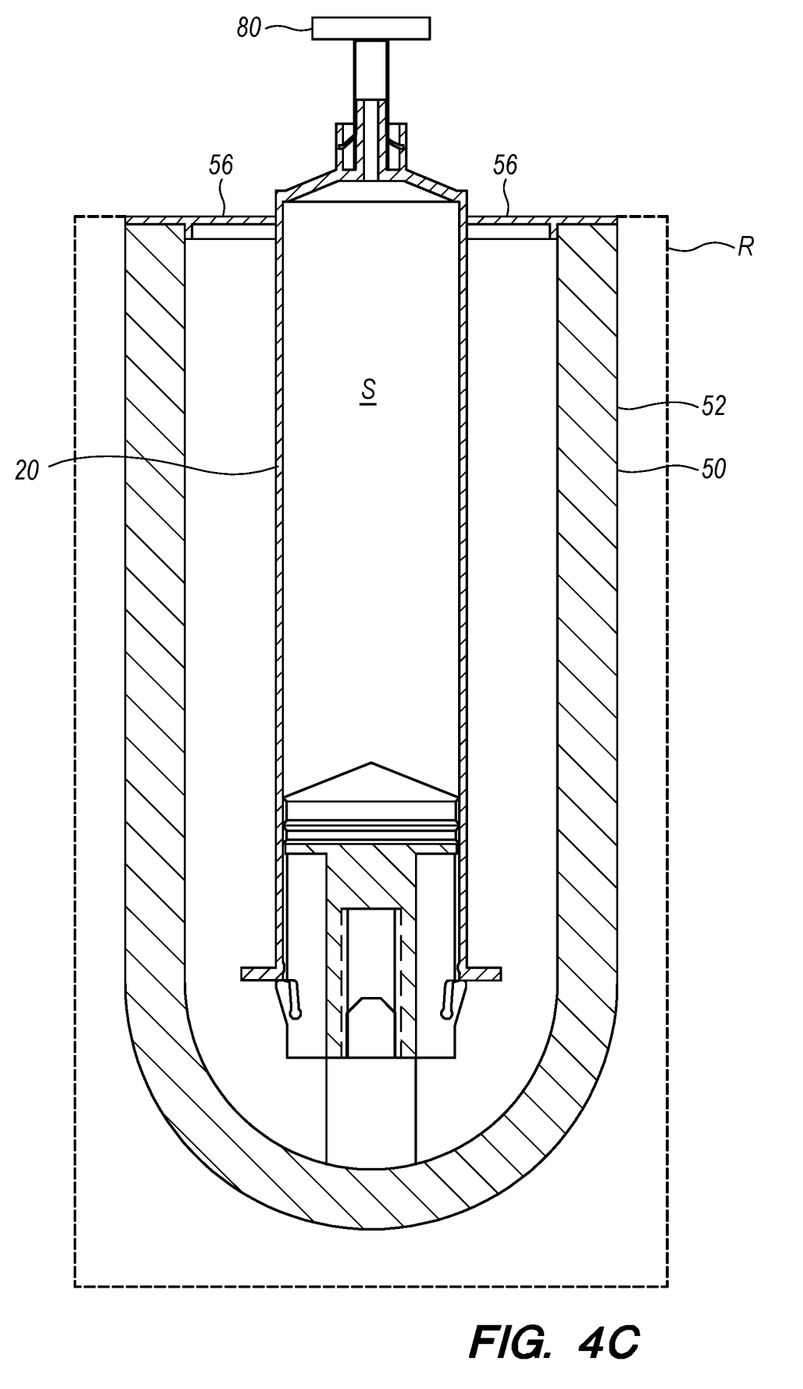
FIG. 4C illustrates a plan cross-sectional view of the sample collection section of the cell collection apparatus positioned for centrifuging employing the retaining cup.

FIG. 4C illustrates the sample collection section 20 of the cell collection apparatus 10 positioned for centrifuging sample S. In an alternative preferred embodiment, cap 80 could be used to seal section 20. The use of cap 80 is particularly preferred because cap 80 reduces sample S's exposure to air and potential infection causing contaminates. In addition, cap 80 also prevents escape of sample S from sample collection section 20.

Figure 4D:
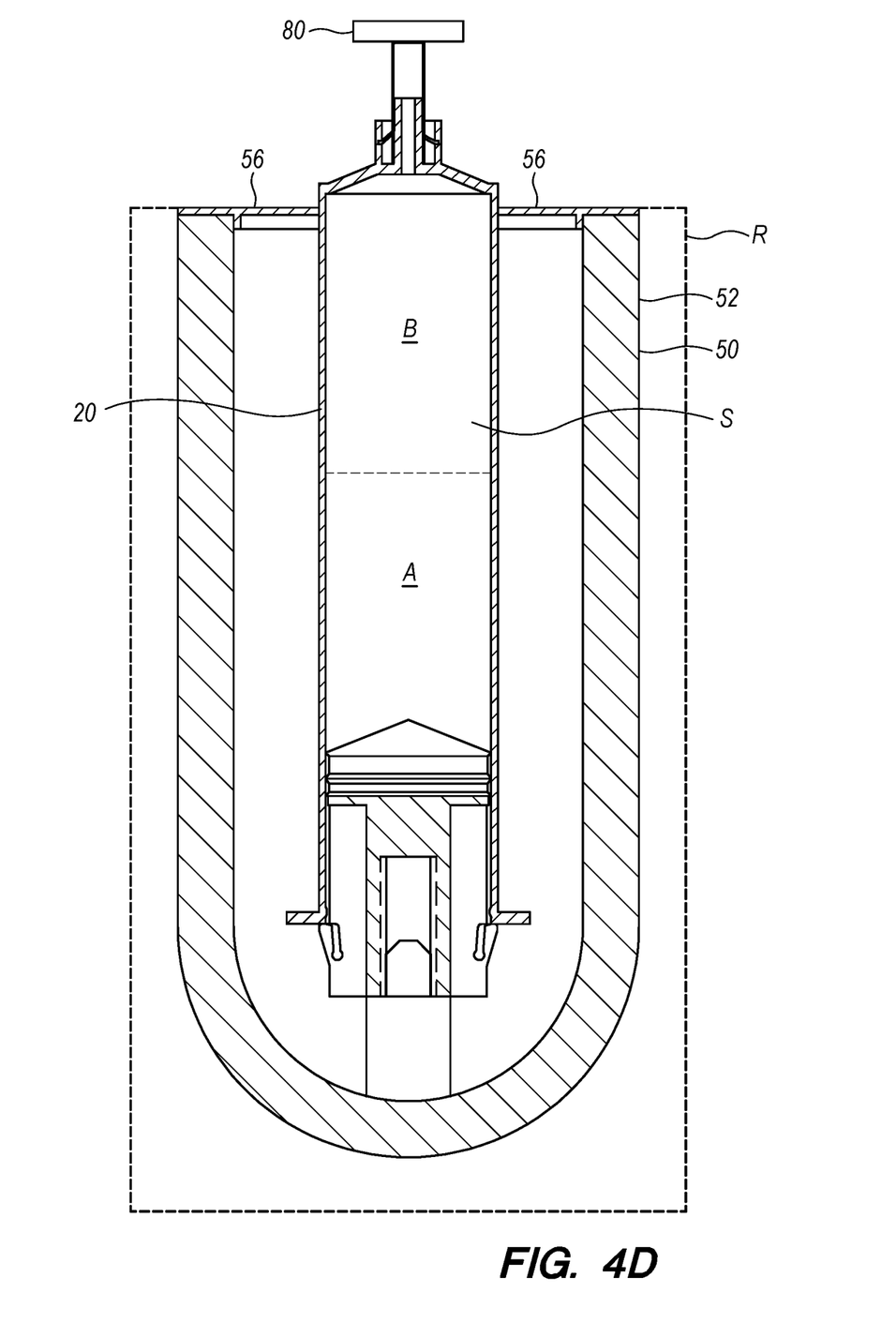
FIG. 4D illustrates a plan cross-sectional view of the sample collection section of the cell collection apparatus after the cell collection apparatus containing a cell sample has been centrifuged employing the retaining cup.

FIG. 4D illustrates sample collection section 20 after centrifuging of a sample S having two components of different densities. As illustrated in FIG. 4D, sample S has separated into its components A and B, by centrifuging. FIG. 4D also illustrates the use of cap 80.

Of course, any sample having components that have different densities could be centrifuged in order to separate sample S into its components. A generic example of this process is illustrated in FIGS. 5A-5F reflecting a generic sample S that has components with three different densities that are, after centrifuging, separated into components A, B, and C. A generic example of how sample S could be separated into three separate components A, B, and C is discussed below. A sample having components of different densities can have its components separated using a centrifuge. The examples given are exemplary and are not limited to a sample with two or three components. Phrased differently, a sample having more than three components, or less than three components, could be separated into its components employing cell collection apparatus 10.

Figure 5A:
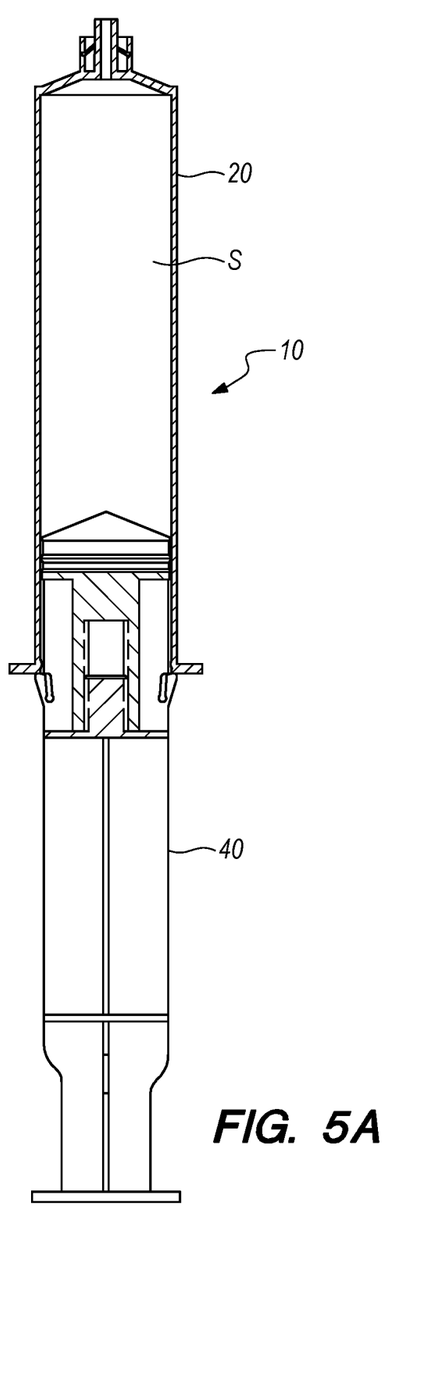
FIG. 5A illustrates a plan cross-sectional view of a generic sample of body fluids before centrifuging.
Figure 5B:
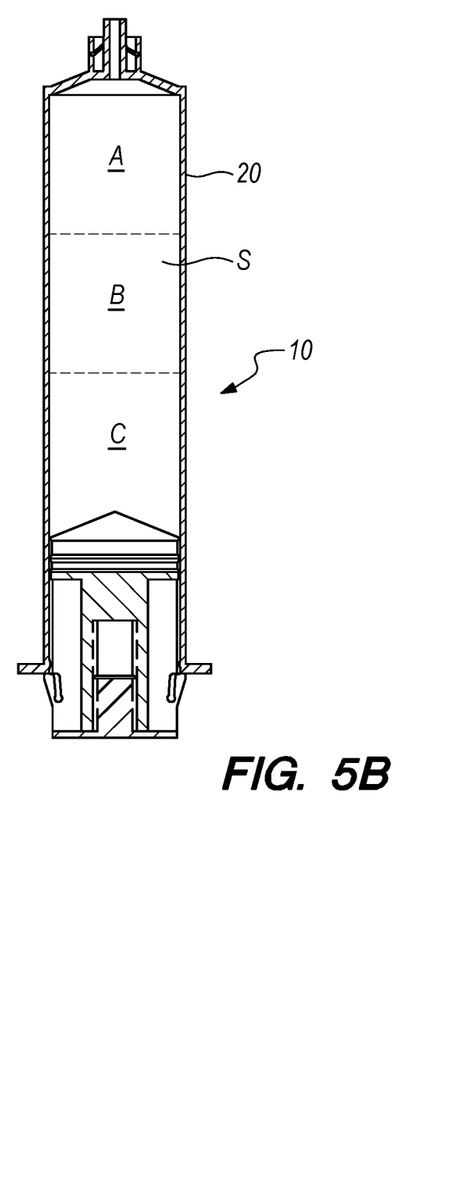
FIG. 5B illustrates a plan cross-sectional view of the centrifuged sample and also illustrates that the sample has divided into components having different densities.

As an example, as illustrated in FIG. 5A, any sample S can be separated, assuming its components have different densities, into the sample's component parts. FIG. 5B illustrates a generic sample S that has been centrifuged and separated into component A, component B, and component C. Sample collection section 20 is detached from detachable section 40 before centrifuging.

Figure 5C:
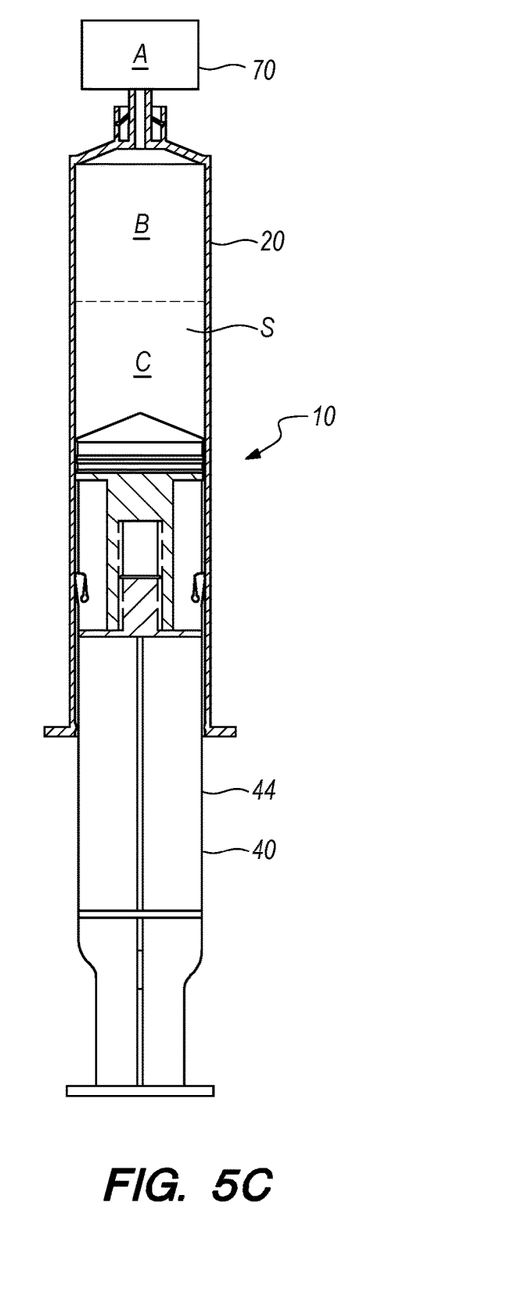
FIG. 5C illustrates a plan cross-sectional view of a first sample component urged into a container

FIG. 5C illustrates sample S after centrifuging has separated sample S into component A, component B, and component C within sample collection section 20 and after sample collection section 20 has been reattached to detachable section 40. As illustrated in FIG. 5C, plunger 44 has urged component A into container 70.

Figure 5D:
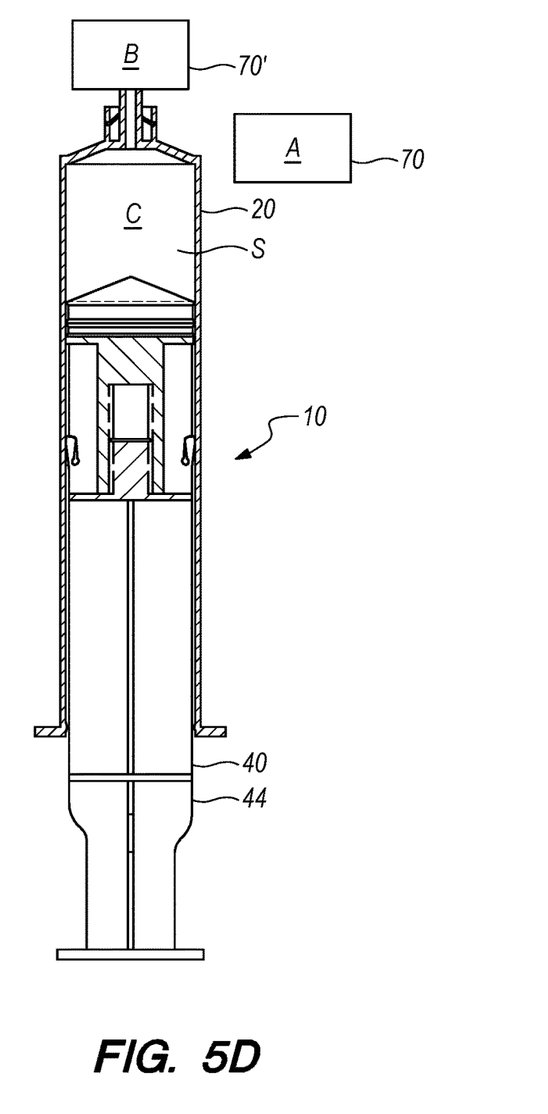
FIG. 5D illustrates a plan cross-sectional view of a second sample component urged into a container.

FIGS. 5C and 5D illustrate that plunger 44 can be depressed to urge component A of sample S into a storage container 70. By way of example only, component A could be urged into storage container 70. Similarly, plunger 44 could be further depressed to urge component B into storage container 70'.

Figure 5E:
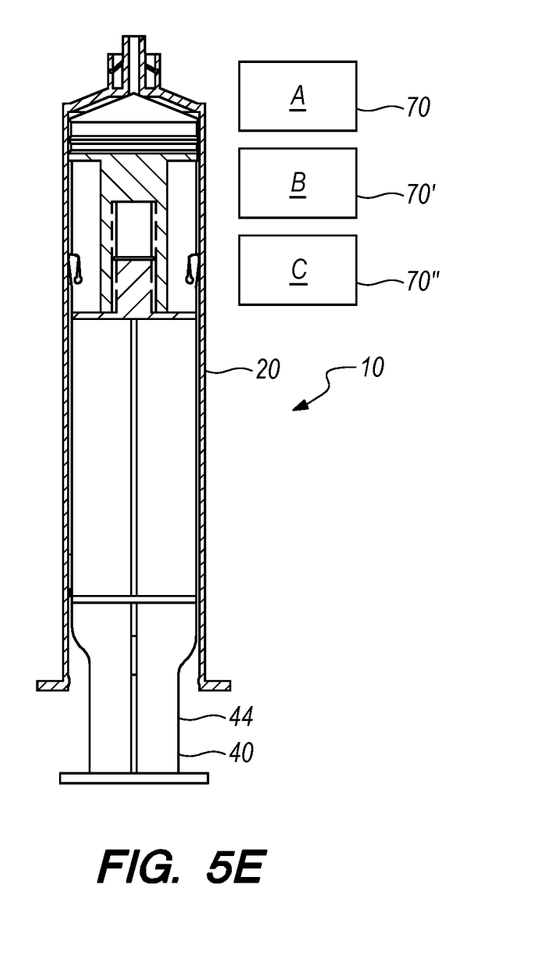
FIG. 5E illustrates a plan cross-sectional view of a third sample component urged into a container.

FIG. 5E illustrates that plunger 44 can be still further depressed to urge component C into storage container 70". Thus, components A, B, and C, have been isolated into separate containers. In other words, FIG. 5E illustrates component A stored within storage container 70 and component B stored within storage container 70' and component C stored within storage container 70". This process could be used to isolate each of the components of sample S into its own storage container and is not limited to a sample having three components.

Figure 5F:
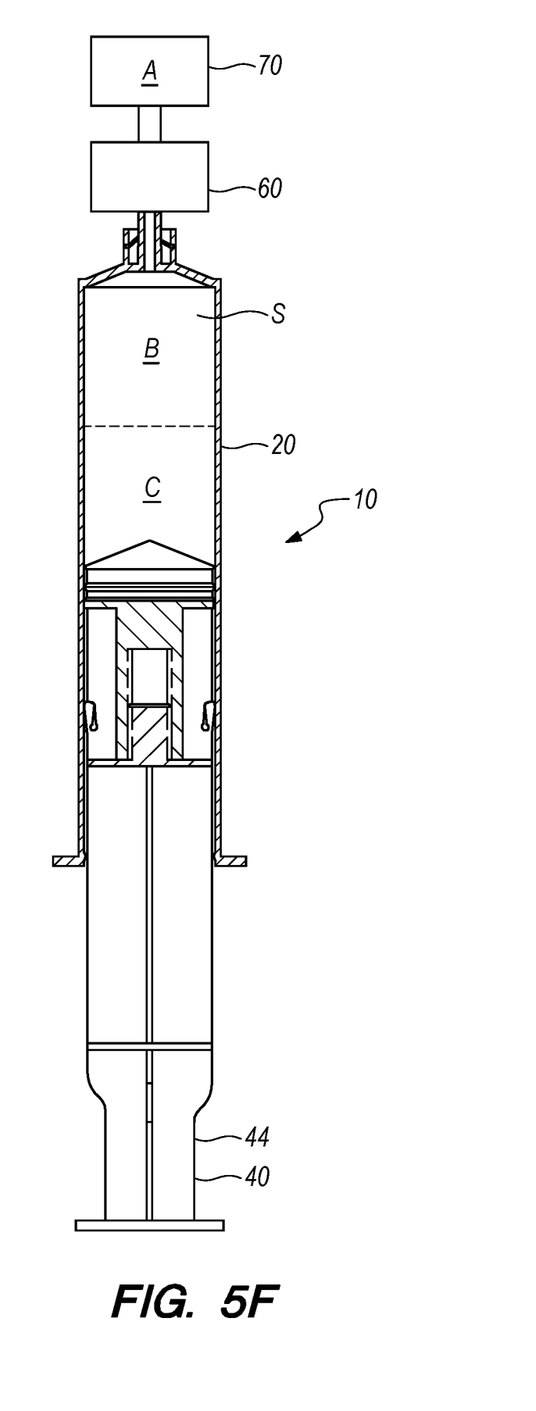
FIG. 5F illustrates a plan cross-sectional view of an alternative embodiment of employing an intermediate section to ensure that the components of the sample are appropriately separated.

FIG. 5F illustrates an alternative embodiment of cell collection apparatus 10 further comprising intermediate action 60. As illustrated in FIG. 5F, component B of sample S is within sample collection section 20. Intermediate section 60 has been placed in fluid connection with sample collection section 20 and storage container 70. Preferably, intermediate section 60 would be clear to allow a user to ensure that storage container 70 contained substantially only sample A and that component B had not been inadvertently urged into sample container 70. Component A could be re-injected into patient P or stored in storage container 70. Similarly, a fresh intermediate section 60 could be used to ensure that components B and C are not inadvertently mixed during transfer to their respective storage container.

Figure 6:
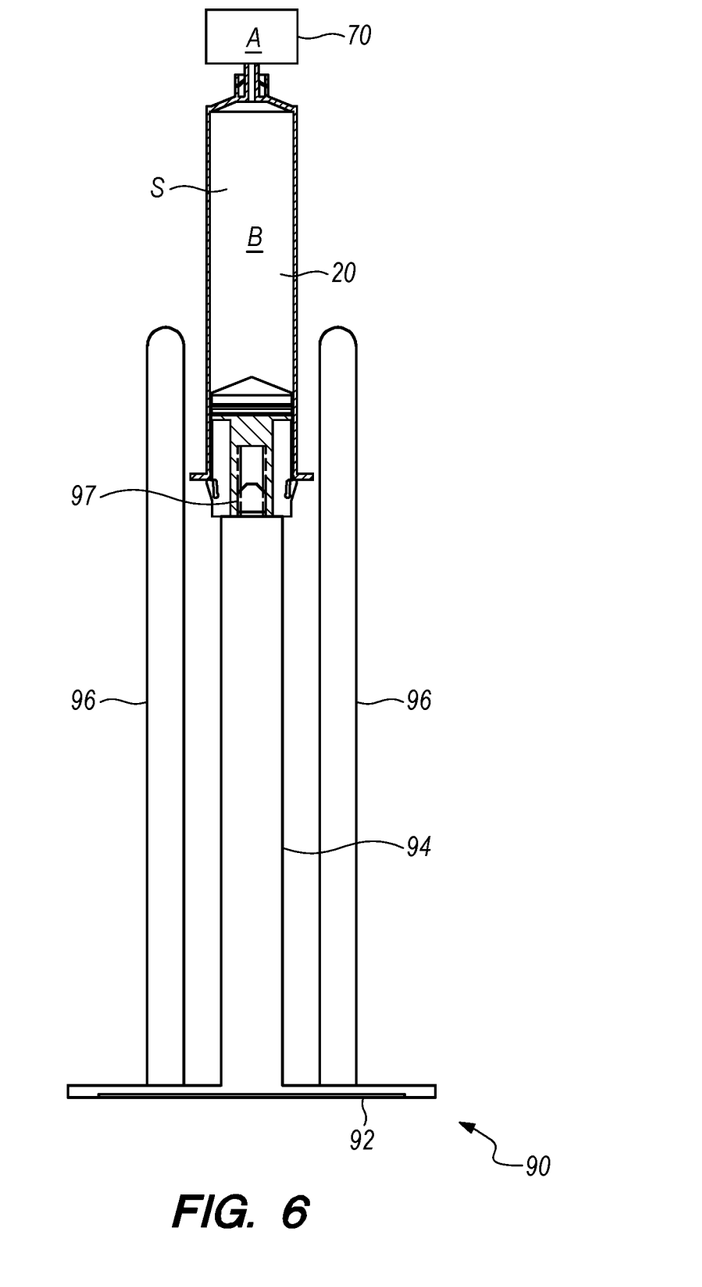
FIG. 6 illustrates a plan cross-sectional view of a transfer support apparatus.

FIG. 6 illustrates a sample S that has been centrifuged and separated into component A and component B. FIG. 6 illustrates that after centrifuging, component A and component B are contained within sample collection section 20. FIG. 6 also illustrates that transfer support apparatus 90 comprises base 92, support 94 and uprights 96. Transfer support apparatus 90 permits a user to support sample collection section 20 and more precisely urge the components out of cell collection section 20. For example, after sample S that has been centrifuged and separated into component A and component B, FIG. 6 illustrates that component A and component B are contained within sample collection section 20. When sample collection section 20 is held by support 94, a user may more precisely dispense component A into sample container 70. This is superior to manually holding the cell collection apparatus 10 and urging the components into a storage container 70 because sample collection section 20 is held steady by transfer support apparatus 90. In addition, it is preferable to minimize movement of sample collection section 20 during transfer of components to storage containers because reducing or eliminating movement of section 20 reduces or eliminates potential remixing of the components of the sample.

While the invention has been illustrated and described in detail in the drawings and description, the same is to be considered as an illustration and is not limited to the exact embodiments shown and described. All equivalents, changes and modifications that come within the spirit of the invention are also protected by the claims that are set forth below.

What I claimed is:

1. A cell collection apparatus for collecting and isolating a sample, comprising:
    a sample collection section, comprising:
        a reservoir barrel with an interior diameter, the reservoir barrel having a proximal end and a distal end, and a flange located at the distal end;
        a single-piece fitting slidably movable within the full longitudinal length of the interior diameter of the reservoir barrel, the single-piece fitting having a proximal side and a distal side, with a post located on the proximal side and a proximal attachment located on the distal side, the single-piece fitting further comprising a clip, the clip selectively positionable to temporarily immobilize the fitting to overcome negative pressure that occurs when the sample is drawn into the reservoir barrel, wherein when the clip is outwardly extended and under the negative pressure, it contacts a distal side of the flange of the reservoir barrel, thereby temporarily immobilizing the fitting;

a seal detachably seated on the post, wherein the seal prevents leakage of the sample, the single-piece fitting slidably movable such that the seal is able to contact the proximal end of the reservoir barrel; and, a detachable section, comprising:

a plunger, the plunger detachably and reattachably connectable to the proximal attachment by a distal attachment, the plunger configured to be both detachable and reattachable from the proximal attachment when the single-piece fitting is entirely within the reservoir barrel and the seal is contacting the proximal end of the reservoir barrel; wherein after detachment of the detachable section, the sample collection section is configured to be centrifuged.

2. The cell collection apparatus of claim 1, wherein the proximal attachment and the distal attachment are threaded, thereby detachably and threadedly connecting the solid fitting and the plunger.

3. The cell collection apparatus of claim 1, further comprising:

a nipple suitable to attach a cannula for collecting the sample from the patient.

4. The cell collection apparatus of claim 1, further comprising:

a nipple suitable to attach a needle for collecting the sample using venipuncture.

5. The cell collection apparatus of claim 1, wherein the clip is a pair of opposing clips and wherein the clips temporarily immobilize at least a portion of the solid fitting within the reservoir barrel.

6. The cell collection apparatus of claim 5, wherein the clips are outwardly biased when within the reservoir barrel.

7. The cell collection apparatus of claim 6, wherein the clips are pliable such that when moved inwardly the fitting is slidably movable within the reservoir barrel.

8. The cell collection apparatus of claim 7, wherein the clips are deformable both inwardly and outwardly.

9. The cell collection apparatus of claim 6, wherein when the clips are positioned inwardly, the fitting is not immobilized and is slidably movable within the reservoir barrel.

10. The cell collection apparatus of claim 2, wherein the threads of the distal attachment are threadedly received by the threads of the proximal attachment such that the distal attachment and the proximal attachment are threadedly and detachably connected.

11. The cell collection apparatus of claim 1, wherein a male-female connector, a reverse male-female connector, a snap, or another clip detachably connect the proximal attachment and the distal attachment.

12. The cell collection apparatus of claim 1, wherein the clip of the cell collection apparatus is formed of a resilient plastic.

* * * * *